(12) United States Patent
Mukundan et al.

(10) Patent No.: US 8,859,268 B2
(45) Date of Patent: Oct. 14, 2014

(54) QUANTITATIVE MULTIPLEX DETECTION OF PATHOGEN BIOMARKERS

(75) Inventors: Harshini Mukundan, Los Alamos, NM (US); Hongzhi Xie, Portland, ME (US); Basil I. Swanson, Los Alamos, NM (US); Jennifer Martinez, Dixon, NM (US); Wynne K. Grace, Taos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 746 days.

(21) Appl. No.: 12/924,929

(22) Filed: Oct. 8, 2010

(65) Prior Publication Data
US 2011/0117585 A1   May 19, 2011

Related U.S. Application Data

(60) Provisional application No. 61/249,940, filed on Oct. 8, 2009.

(51) Int. Cl.
*C12M 1/34* (2006.01)
*G01N 33/543* (2006.01)
*G01N 21/77* (2006.01)
*G01N 21/55* (2014.01)

(52) U.S. Cl.
CPC ........ *G01N 33/54373* (2013.01); *G01N 21/774* (2013.01); *G01N 21/553* (2013.01)
USPC .......... 435/288.7; 385/12; 385/129; 385/130; 385/132; 422/82.11; 436/524

(58) Field of Classification Search
None
See application file for complete search history.

(56) References Cited

U.S. PATENT DOCUMENTS

| | | | | |
|---|---|---|---|---|
| 5,492,840 | A | * | 2/1996 | Malmqvist et al. ........... 436/518 |
| 5,631,170 | A | * | 5/1997 | Attridge ......................... 436/518 |
| 7,927,789 | B1 | * | 4/2011 | Baird et al. ....................... 435/4 |

* cited by examiner

*Primary Examiner* — Chris L Chin
(74) *Attorney, Agent, or Firm* — Bruce Cottrell

(57) ABSTRACT

The present invention addresses the simultaneous detection and quantitative measurement of multiple biomolecules, e.g., pathogen biomarkers through either a sandwich assay approach or a lipid insertion approach. The invention can further employ a multichannel, structure with multi-sensor elements per channel.

2 Claims, 10 Drawing Sheets

Table 1

| Channel | Background | Coupling Efficiency (%) | S565QD-10 pM | Average | Sdev | %CV |
|---|---|---|---|---|---|---|
| A1 | 125 | 41 | 3750 | 3612.5 | 978.6 | 27.1 |
| A2 | 225 | 32 | 5000 | | | |
| A3 | 175 | 25 | 3200 | | | |
| A4 | 190 | 44 | 2500 | | | |
| B5 | 180 | 27 | 3250 | 3025 | 798.7 | 26.4 |
| B6 | 210 | 35 | 3500 | | | |
| B7 | 250 | 35 | 3600 | | | |
| B8 | 150 | 48 | 1750 | | | |
| C9 | 190 | 30 | 2500 | 3112.5 | 855.5 | 27.5 |
| C10 | 200 | 28 | 4000 | | | |
| C11 | 300 | 40 | 3800 | | | |
| C12 | 240 | 48 | 2150 | | | |
| Average | 203 | 36 | 3250 | | | |
| Sdev | 46 | 8 | 882 | | | |
| %CV | 23 | 22 | 27 | | | |

Table 2:

| Channel | PA | LF | Normalized_PA | Normalized_LF |
|---|---|---|---|---|
| A1 | 4600 | 8250 | 122.7 | 220.0 |
| A2 | 5100 | 4750 | 127.5 | 168.8 |
| A3 | 2597 | 10882 | 81.2 | 246.3 |
| A4 | 3592 | 6570 | 102.6 | 187.7 |
| B5 | 3556 | 0 | 109.4 | 0.0 |
| B6 | 3806 | 0 | 108.7 | 0.0 |
| B7 | 2866 | 0 | 79.6 | 0.0 |
| B8 | 2009 | 0 | 114.8 | 0.0 |
| C9 | 0 | 9180 | 0.0 | 204.0 |
| C10 | 0 | 7650 | 0.0 | 191.3 |
| C11 | 0 | 10360 | 0.0 | 193.7 |
| C12 | 0 | 6690 | 0.0 | 279.6 |
| Average | 3515.8 | 8041.5 | 105.8 | 211.4 |
| Sdev | 1022.2 | 2062.0 | 17.6 | 36.1 |
| %CV | 29.1 | 25.6 | 16.6 | 17.1 |

FIGURE 5

QUANTITATIVE MULTIPLEX DETECTION OF PATHOGEN BIOMARKERS

CROSS REFERENCE TO RELATED APPLICATION

This application claims the benefit of priority of U.S. Provisional Patent Application 61/249,940, filed 8 Oct. 2009, and incorporated herein in its entirety.

STATEMENT REGARDING FEDERAL RIGHTS

This invention was made with government support under Contract No. DE-AC52-06NA25396, awarded by the U.S. Department of Energy. The government has certain rights in the invention.

BACKGROUND OF INVENTION

The invention relates to the simultaneous detection of multiple pathogen biomarkers. More particularly, the invention relates to the quantitative simultaneous detection of multiple pathogen biomarkers.

Biomarkers are loosely defined as bio-molecules that are differentially expressed during disease. In infectious disease, these may be pathogen-associated molecules that are secreted in the host. In malignant conditions such as cancer, these are host molecules whose expression levels are changed during disease. In either case, the differential expression of biomarkers is indicative of disease. Often, the secretion or expression of these biomarkers supersedes other pathological changes in the host, potentially allowing for very early detection of the disease. Despite these advantages, biomarkers are not routinely used for disease detection for several reasons: 1) circulating concentrations of biomarkers are very low, requiring ultra-sensitive detection technology, 2) most detection platforms are influenced by non-specific interactions in complex biological samples such as serum and urine, 3) most of the available technologies are not capable of accurate quantitation of biomarker concentrations, and 4) no single biomarker can be used for accurately predicting disease in all stages of infection. These problems have limited the development of biomarker-based detection strategies. Indeed, many of the popular diagnostic assays (e.g. enzyme-linked immunoSPOT or EliSpot test for tuberculosis) measure the immune response of the host to secreted pathogen biomarkers because the former are easier to measure and quantitate. An ideal biomarker-based detection strategy should be capable of the simultaneous and ultra-sensitive detection of a limited suite of such biomolecules in complex biological samples.

As no single biomarker can accurately predict disease, an ideal strategy should be capable of the sensitive detection of a limited suite of such biomolecules. It was attempted to achieve multiplex detection by using photostable and tunable quantum dots (QDs) as the fluorescence reporters in our experimental platform. QDs have been extensively used for biological applications such as DNA sorting, measuring protein-protein interactions, enzyme assays, in situ hybridization experiments and others. Compared to organic dyes, QDs provide several advantages that make them amenable for use in an immunoassay platform. QDs have broad absorption bands with high extinction coefficients, narrow and symmetric emission bands with high quantum yields, and excellent photostability8. Perhaps the most significant advantages of QDs to multiplex detection platforms is their broad Stoke's shift, which facilitates the simultaneous excitation of several distinct QDs at a single excitation wavelength. The size-based optical 'tenability' of QDs, when combined with their other advantages, makes them ideal candidates for use in biological applications such as as in the present invention. Indeed, it has been said that 'multiplex detection platforms is where QDs will have their maximum application in the near future'. More recently, antibodies conjugated with dihydroxylipoic acid (DHLA) capped QDs have been used in plate-based immunoassays for protein toxins. That approach allowed the simultaneous detection of four protein toxins with reasonable sensitivity. However, this technology suffers from the drawbacks of traditional plate-based immunoassays such as poor sensitivity, high non-specific binding and insufficient quantitation. Further, DHLA QDs are associated with low quantum efficiency and are unstable at neutral pH, limiting their application to bio-assays in general.

SUMMARY OF INVENTION

The present invention provides a method of simultaneously detecting and quantitatively measuring multiple pathogen biomolecules including: (a) contacting a target sample containing multiple differing target pathogen molecules with a sandwich assay element including a substrate, a patterned waveguide upon the substrate, a film layer upon the patterned waveguide, a biomolecule including an attached inorganic fluorescent reporter molecule, the biomolecule attached to the film layer as an assay element standard, an amount of at least one recognition ligand attached to the film layer for capture of at least two differing target pathogen molecules, each pathogen molecule having at least two binding sites, the capture at one of the binding sites, (b) maintaining the target sample together with the sandwich assay element for a time sufficient for a binding event to occur between target pathogen molecules within the sample and the at least one recognition ligand adapted for capture of at least two differing target pathogen molecules, (c) washing excess biological target from contact with the sandwich assay element, (d) contacting the sandwich assay element with an amount of at least two additional recognition ligands each attached to a different inorganic fluorescent reporter molecule, each additional recognition ligand adapted for binding at a second binding site of a specifically targeted pathogen molecule, (e) washing excess of the at least two additional recognition ligands from contact with the sandwich assay element, (f) interrogating the sandwich assay element with excitation light from the waveguide, and, (g) obtaining an output correlated to detection and quantitative measurement of target pathogen molecules within the target sample.

In another embodiment of the present invention is provided a method of simultaneously detecting and quantitatively measuring multiple pathogen biomolecules characterized by having a lipophilic portion of sufficient size and chemical composition for insertion into a lipid bilayer, the method including: (a) contacting a target sample containing multiple differing target pathogen biomolecules with an assay element including a substrate, a patterned waveguide upon the substrate, a lipid bilayer upon the patterned waveguide, a biomolecule including an attached inorganic fluorescent reporter molecule, the biomolecule attached to the lipid bilayer as an assay element standard, (b) maintaining the target sample together with the assay element for a time sufficient for a insertion event to occur between target pathogen biomolecules characterized by having a lipophilic portion of sufficient size and chemical composition for insertion into a lipid bilayer within the sample and the lipid bilayer, (c) washing excess biological target sample from contact with the assay element, (d) contacting the assay element with an amount of at least two additional recognition ligands each attached to a different inorganic fluorescent reporter molecule, each additional recognition ligand adapted for binding to a specifically targeted pathogen biomolecule, (e) washing excess of the at least two additional recognition ligands from contact with the assay element, (f) interrogating the assay element with excitation light from the waveguide, and, (g) obtaining an output correlated to detection and quantitative measurement of target pathogen biomolecules within the target sample.

One aspect of the present invention is to provide sandwich assay element including: (a) a substrate, (b) a patterned waveguide upon the substrate, (c) a film layer upon the patterned waveguide, (d) a biomolecule including an attached inorganic fluorescent reporter molecule, the biomolecule attached to the film layer as an assay element standard, and, (e) at least one additional recognition ligand attached to the film layer for capture of a first target pathogen molecule having at least two binding sites.

Another aspect of the invention is to provide assay element including: (a) a substrate, (b) a patterned waveguide upon the substrate, (c) a lipid bilayer upon the patterned waveguide, and, (d) a biomolecule including an attached inorganic fluorescent reporter molecule, the biomolecule attached to the lipid bilayer as an assay element standard.

Another aspect of the invention is to provide kit for simultaneous detection and quantitative measurement of multiple pathogen biomarkers, the kit including: (1) a sandwich assay element including a substrate, a patterned waveguide upon the substrate, a film layer upon the patterned waveguide, a biomolecule including an attached inorganic fluorescent reporter molecule, the biomolecule attached to the film layer as an assay element standard, an amount of at least one recognition ligand attached to the film layer for capture of at least two differing target pathogen molecules, each pathogen molecule having at least two binding sites, the capture at one of the binding sites; and (2) an amount of at least two additional recognition ligands each attached to a different reporter molecule and each additional recognition ligand adapted for binding at a second of the binding sites of one specifically targeted pathogen molecule.

Still another aspect of the invention is to provide a kit for simultaneous detection and quantitative measurement of multiple pathogen biomolecules characterized by having a lipophilic portion of sufficient size and chemical composition for insertion into a lipid bilayer, the kit including: (1) a assay element including a substrate, a patterned waveguide upon said substrate, a lipid bilayer upon the patterned waveguide, a biomolecule including an attached inorganic fluorescent reporter molecule; and (2) an amount of at least two additional recognition ligands each attached to a different reporter molecule and each additional recognition ligand adapted for binding to one specifically targeted pathogen molecule.

Yet another aspect of the present invention is to provide a multichannel structure for use in simultaneous detection and quantitative measurement of multiple pathogen biomarkers, the structure including: a substrate having at least one fluid channel therein wherein each fluid channel has at least two sensing element regions per channel, said multichannel structure further including a light absorbing material situated around each individual sensing element region thereby essentially eliminating cross-talk coupling between sensing element regions, each sensing element region having: (a) a film layer upon the substrate and (b) a biomolecule including an attached inorganic fluorescent reporter molecule, the biomolecule attached to said film layer as an assay element standard; and, at least one additional recognition ligand attached to said film layer for capture of a target pathogen molecule having at least two binding sites.

These and other aspects, advantages, and salient features of the present invention will become apparent from the following detailed description, the accompanying drawings, and the appended claims.

BRIEF DESCRIPTION OF THE DRAWINGS

FIG. 1 shows a photograph of the multichannel waveguide assembled in a flow cell. Laser light (532 nm excitation) is coupled into grating B2. The bright spot is the incident laser beam being coupled into the waveguide via the refractive holographic grating coupling element and the streak to the left is the propagation of the incoupled light by total internal reflection.

FIGS. 2c and 2d demonstrates plate-based fluorescence sandwich immunoassays for PA and LF using the labeled conjugates as the reporter. The LoD in each case, in serum, was found to be 100 pM, higher than that achieved by the waveguide-based platform (FIG. 3). All data are plotted as mean±standard deviation of three independent measurements.

FIG. 5 shows tables including summary measurement of the waveguide-associated background, coupling efficiency (uncoupled power is 440 μW in all channels) and the signal observed with 10 pM S-565QD (internal standard) is indicated for one multichannel waveguide.

DETAILED DESCRIPTION

Figure 1A:
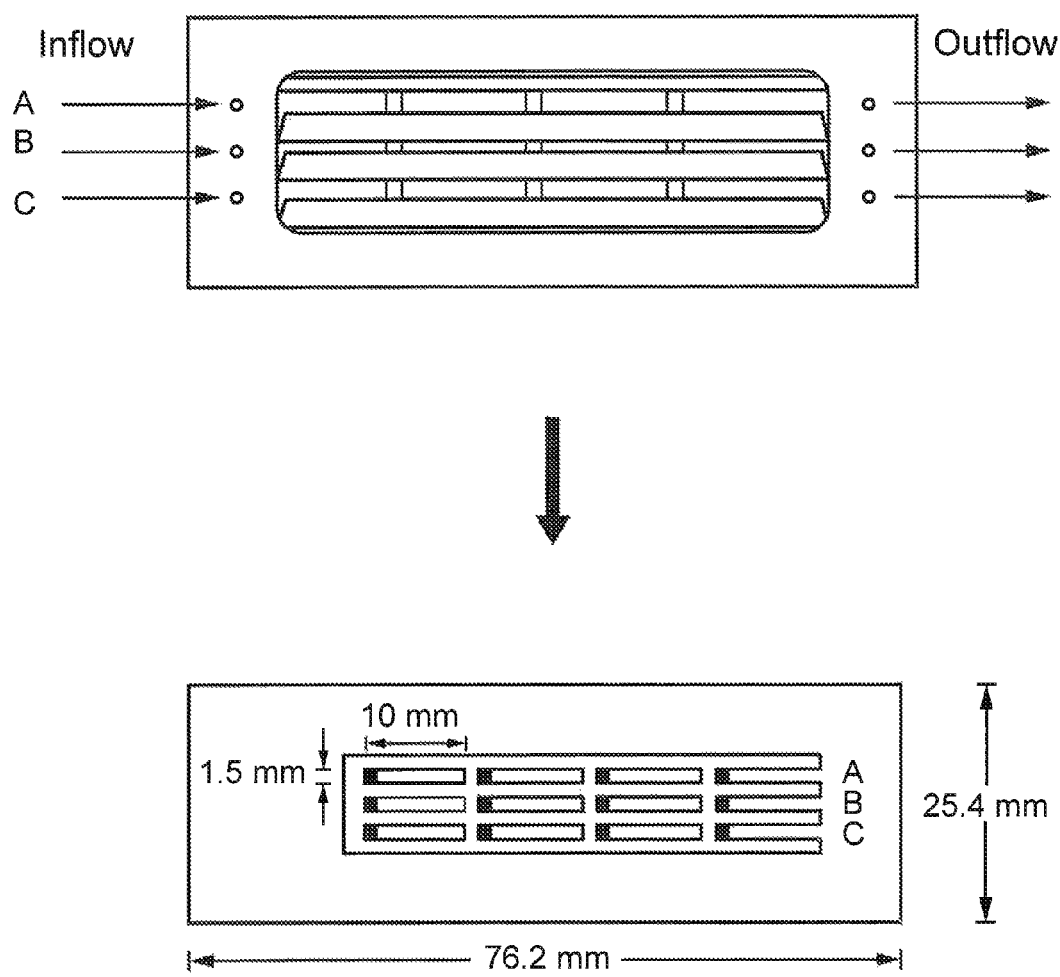
FIG. 1A (bottom panel) is a schematic representation of the multichannel waveguide (not to scale). Dimensions of the individual sensing elements are indicated. The colored squares represent the refractive holographic grating couplers etched into each sensing element. The channels and each sensing elements have a chrome absorbing material surrounding them, permitting each sensing element to be excited independently with out cross talk or inadvertent coupling between the sensing elements. The chrome absorbing material is represented by the gray mask surrounding each element.

The work presented herein addresses many of the limitations of biomarker-detection strategies.

The present invention concerns assay processes using, e.g., a planar optical waveguide and thin film supported assay elements on the planar optical waveguide. In addition to use of a waveguide as a fluorescence transduction approach, the present invention could employ a fiber optic structure or simply direct microscopic imaging with excitation provided in any number of well known ways.

The base substrate in the present invention is a waveguide, in some instances preferably a single mode planar optical waveguide. Single mode waveguides can be generally formed from thin (generally from about 100 to 150 nm in thickness) high index of refraction dielectric materials deposited upon a substrate having a much lower refractive index. Use of a waveguide can eliminate some problems related to background autofluorescence from complex samples and Raman scattering from water. Preferably, the waveguide surfaces will be of a material that can be employed to attach an intervening thin film material, such materials including, e.g., silica, silicon nitride, titania, mixtures of silica and silicon nitride often referred to as SiON, and the like. Diffraction gratings, etched into the substrate, provide a facile method of coupling laser light into the thin waveguide film.

The present invention involves the use of recognition ligands bound to a film on the base substrate or waveguide. By "recognition ligand" is meant any compound, composition, molecule or ligand capable of recognizing and having a binding affinity for a specific target. Natural recognition molecules include antibodies, enzymes, lectins, and the like. For example, the recognition molecule for an antigen is an antibody while the recognition molecule for an antibody is either an anti-antibody or preferably, the antigen recognized by that particular antibody.

In sandwich assay sensors such as the present invention, recognition ligands are sometimes referred to as capture ligands. Among such ligands capable of recognizing and having a binding affinity for a specific target are biomolecules such as antibodies, antibody fragments, i.e., a portion of a full length antibody such as, e.g., Fab, Fab', F(ab')$_2$, or Fv fragments and the like, recombinant or genetically engineered antibody fragments, e.g., diabodies, minibodies and the like. Other suitable recognition ligands may include peptoids, single chain Fv molecules (scFv), peptides and mimetics thereof, carbohydrates, sugars and mimetics thereof, oligosaccharides, proteins, nucleotides and analogs thereof, aptamers, affinity proteins, small molecule ligands, receptor groups and monomers of multimers of each, i.e., multidentate ligands. Mixtures of such recognition ligands may be used as well.

The base substrate includes a film thereon, the film being a bilayer membrane, a hydrid bilayer membrane, a polymerized bilayer membrane, or a self assembled monolayer (SAM) containing polyethylene glycol or polypropylene glycol groups therein. The term "polymerized membrane" refers to membranes that have undergone partial or complete polymerization. One example of a polymerized membrane can be polymerized phospholipids prepared from polymerizable monomaniac groups as shown, e.g., in U.S. Pat. No. 6,699,952.

When a bilayer membrane, e.g., a lipid bilayer is used, capture of a target biomarker or pathogen biomolecule may be accomplished directly without any capture agent. This can occur if the pathogen biomolecules are characterized by having a lipophilic portion of sufficient size and chemical composition for insertion into a lipid bilayer. Such a lipid capture or lipid insertion approach is described in Provisional Patent Application 61/206,980 for "Lipid Insertion for Antigen Capture and Presentation and Use as a Sensor Platform" filed on Feb. 6, 2009, by Mukundan et al, such details herein incorporated by reference.

By "membrane" is generally meant supported bilayers where membrane layers are deposited upon a support surface, hybrid bilayers where a first layer is covalently attached to an oxide surface, tethered bilayers where a membrane molecule is covalently bonded to the oxide substrate, or bilayers cushioned by a polymer film. Supported membranes useful in the practice of the present invention are generally described by Sackmann, in "Supported Membranes: Scientific and Practical Applications", Science, vol. 271, no. 5245, pp. 43-45, Jan. 5, 1996.

A self assembled monolayer can be attached to the substrate as follows: solution or vapor deposition using siloxane groups such as octadecyltrichlorosilane (OTS) or by Langmuir-Blodgett assembly using a LB trough.

The lipid components that can be used for the membrane layers in the present invention are generally described in the literature. Generally, these are phospholipids, such as, for example, phosphatidylcholines, phosphatidylethanolamines, phosphatidylglycerols, phosphatidylserines, phosphatidic acids, phosphatidylinositols or sphingolipids.

The recognition ligands can be linked or bound through various molecules to the film on the waveguide surface. Among suitable linking molecules can be various biotin-avidin linkages such as biotinylated lipids, and trifunctional linker molecules as described by Schmidt et al., U.S. Ser. No. 10/104,158, "Generic Membrane Anchoring System", filed on Mar. 21, 2002, such description incorporated herein by reference. Such trifunctional linker molecules can include membrane anchoring groups where the film is a membrane. Such trifunctional linker molecules can be preferable where a reference dye is desired to be incorporated into the system by addition onto one arm of the trifunctional linker molecules. This can serve to minimize background by comparison with the dye label on the sandwich assay. Such trifunctional linkers may also have a secondary recognition ligand in addition to the primary recognition ligand. The use of a secondary recognition ligand that binds an orthogonal epitope relative to the primary recognition ligand can serve to enhance the effective binding affinity thereby increasing the overall sensitivity of the assay.

The sandwich assay process of the present invention can be used for the determination, either qualitative or, mostly, quantitative, of biomolecules, whether bio pathogens or other types of biomolecules.

In one embodiment of the invention, a waveguide based optical biosensor platform for the sensitive and specific detection of biomarkers associated with disease has now been developed. The application of this technology to the detection of biomarkers associated with diseases such as anthrax, influenza, breast cancer and tuberculosis has been previously validated (unpublished data). The exponential decay of the evanescent wave within 200-400 nm from the waveguide surface allows for spatial filtering, thereby minimizing autofluorescence associated with complex samples such as serum. By this mechanism, only molecules bound on the waveguide surface are excited, whereas fluorescent solution contaminants are not detected. This allows for the minimization of non-specific interactions, especially when complex biological samples, which may be autofluorescent, are considered. Further, optimal silane-based surfaces for waveguide functionalization that minimize non-specific binding in complex patient samples have been developed. Additionally, this technology has been successfully evaluated for the detection of breast cancer biomarkers in patient serum and nipple aspirate fluid samples and obtained 100% corroboration with disease progression in a blind study.

The present invention has attempted to overcome previous disadvantages by 1) performing the immunoassays on a functionalized waveguide, thereby allowing for excellent sensitivity, low non-specific binding, and accurate quantitation, and 2) using polymer coated QDs that are stable at neutral pH and hence, better suited for biological applications.

To facilitate assay reproducibility and to increase the throughput of samples processed at a given time, a multichannel waveguide capable of the simultaneous detection of multiple different samples in quadruplicate has been developed. In one aspect of the present invention, the design, fabrication and evaluation of a multichannel waveguide for the sensitive, quantitative multiplex detection of *Bacillus anthracia* antigens—protective antigen (PA) and lethal factor (LF)—in serum using QDs as the fluorescence reporters has been addressed. The present invention relies upon an internal standard such as streptavidin-coated QDs to measure inter- and intra-assay variability. These biomarkers are simply a model system for the demonstration of the feasibility of this detection approach. In theory, the assay can be used for any biomarker for which two recognition ligands are available.

Waveguides used in the present invention were fabricated at nGimat®, Atlanta (see methods). Purified antibodies (mouse monoclonal, IgG1, human adsorbed) that bind orthogonal epitopes of the anthrax PA and LF were obtained from QED Bioscience Inc. Aminofunctionalized QD (655 nm, QD655), Qdot®655 ITK™ carboxyl QDs and AF647-N-hydroxysuccinimide (NHS) ester labeling kits, streptavidin-QD conjugate (S-QD565) and 96 well plates were purchased from Life Technologies (formerly Invitrogen). Biotinylation, protein estimation and electrophoresis reagents were obtained from Pierce. Gel filtration columns and spin filters were from Harvard Apparatus. Buffers, membrane spin filters were from Millipore Inc. and chemicals, immunoblot materials, and other components were purchased from Sigma Aldrich or Fisher Scientific. Materials required for waveguide functionalization are listed in detail elsewhere (see Anderson et al., Langmuir, 2008, 24(5), 2240-2247) such description incorporated herein by reference. Nunc Immunosorp plates for use in immunoassays were purchased from Nalgene Nunc Inc., (Milwaukee, Wis.). Secondary antibodies were purchased from Jackson ImmunoResearch, West Grove, Pa. and Southern Biotech Ltd, Birmingham, Ala. All other immunoassay and protein estimation reagents were purchased from Pierce Biologicals Ltd., Rockford, Ill.

The fabrication and specification of single-mode planar optical waveguides used in the assay of the present invention are described in detail elsewhere (see Martinez et al., J Mater Chem, 2005, 15, 4639-4647, Mukundan et al., Sens. Actuators B Chem. 2009, 138(2) 453-460), and Grace et al., Proc. SPIE—Int. Soc. Opt. Eng: USA, 2004, 55-64) such descriptions incorporated herein by reference. The general requirements for the multichannel waveguide are described below while and the waveguides were prepared at nGimat Co., Atlanta. The waveguide consists of a 76.2 mm diameter, 2 mm thick fused silica optically polished substrate (low refractive index, μ=1.46) and a $Si_3N_4$ high index film (μ=1.81), 110 nm+/−5 nm thick. The very thin film requires the use of refractive grating elements for coupling light into the waveguide. The grating coupler elements are fabricated using a holographic interference technique to generate the periodic pattern prior to the deposition of the waveguide film. For a wavelength of 532 nm and a +10° coupling angle the period is 420 nm. That pattern is etched into the substrate surface by a reactive ion etching process and subsequently over-coated with the $Si_3N_4$. To ensure the gratings are not affected by ambient refractive index changes, the grating coupler region must also be over-coated with a layer of dense $SiO_2$ (1100 nm or thicker), thus isolating the evanescent field from the surrounding media. The actual sensing area is a thin (10 nm) $SiO_2$ film deposited on the $Si_3N_4$ film on the waveguide surface sensing area, which provides the functional surface required for the attachment of self-assembled monolayer or lipid bilayer sensing films.

In one embodiment, a multichannel waveguide consists of three channels with four sensing elements per channel (FIG. 1). Each sensing element is 10 mm long and 1.5 mm wide and has a 1.5 mm×1.5 mm detractive grating element, which enables independent excitation of each sensing element. The channels and sensing elements also have a chrome absorbing material surrounding them, which removes the possibility of cross-talk or inadvertent coupling between the sensing elements. After the waveguide coatings have been deposited onto the substrate, the substrate is cut to its final dimensions (76.2 mm×25.4 mm). Cutting the substrate to these dimensions permits it to be incorporated into a flow cell (specifically designed for these waveguides) and mounted into a holder for use on our waveguide-based optical biosensor (FIG. 1). The design and fabrication of the multichannel waveguide allows for accurate detection in all 12 sensing elements without any fluorescence bleed-through. The injection time is very short (few seconds) with respect to the diffusion time for antigens and reporter antibodies in the injected sample. As a result, each element "sees" the same concentration of target antigens and reporter antibodies. For experiments using a single exposure of sample to the sensing chip, as described below, the total analyte contained within the sample is $\sim 1\times 10^{-17}$ moles for limit of detection (1 pM) noted below for PA and LF.

The waveguide surface was functionalized using self-assembled monolayers (SAMs) as is described in detail elsewhere (Anderson et al., Langmuir, 2008, 24(5), 2240-2247) such description incorporated herein by reference. Briefly, silica surfaces were functionalized by self-assembly of an amine-terminated silane film using vapor-phase deposition of (3-amino-propyl)methyldiethoxysilane. The quality of the monolayer films and uniform surface coverage was determined by ellipsometry and contact angle measurements. The amine-terminated films were chemically modified with a mixture of carboxylic acid-terminated poly(ethylene glycol) (PEG) chains of varying functionality. A fraction of the PEG chains (0.1-10 mol %) were terminated in biotin, which produced a surface with an affinity toward streptavidin. The surface is biotinylated (0.1%) to facilitate the immobilization of a biotinylated capture antibody by biotin-avidin chemistry and allows for the use of a QD-labeled streptavidin, with an emission at 565 nm (S-QD565), as the internal standard.

Figure 1B:
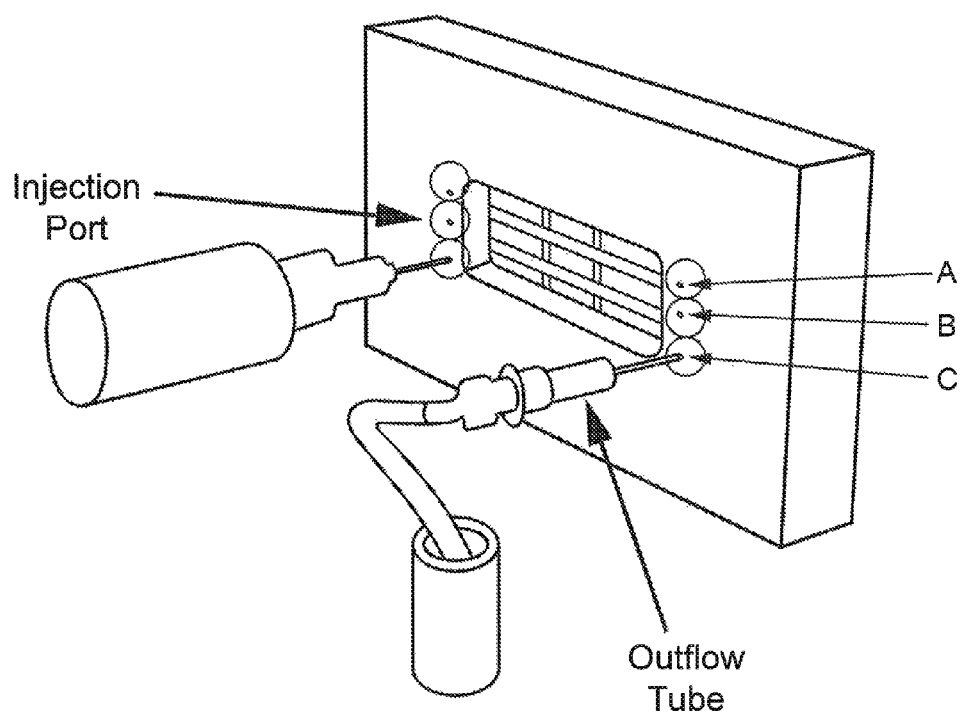
FIG. 1B shows the multichannel waveguide assembled in a specially designed flow cell, which allows the waveguide to be mounted to the instrument, and the ability to inject samples into each channel independently. The injection orientation and the flow channel designations are indicated.

The functionalized single-channel waveguides are assembled into a flow-cell. The functionalized multichannel waveguides require different materials. The flow cell that consists of a three-channel (0.5 mm thick) silicone rubber gasket and a glass cover (76.2 mm×25.4 mm×1 mm) with six holes precisely bored to align individual channels (FIG. 1). In either single or multi-channel arrangements, the flow cell is mounted on a holder with septum material over the holes. The septa form a seal with the glass cover and allow the addition of reagents via a syringe. This configuration minimizes reagent volumes (100 µl/channel), is self-sealing, and allows the addition of multiple reagents.

Preparation of antibodies was as follows. Antibodies that bind orthogonal epitopes of PA and LF were identified from either previous work described by Martinez et al., J Mater Chem, 2005, 15, 4639-4647, such description incorporated herein by reference, or by Geddie et al., J. Biol. Chem. 2005, 280, 35641-35646, such description incorporated herein by reference. The detailed protocols for the biotinylation of the capture antibody have been described elsewhere. Briefly, the capture antibodies were modified by biotinylation using sulfo-NHS biotin (20 molar excess) to allow their immobilization on the waveguide surface. The antibody, in PBS, was mixed with the EZ-Link Sulfo-NHS-biotin and incubated at room temperature for 50 minutes. Free biotin and reagents were removed by size-exclusion chromatography on a Sephadex G25 column. The biotinylated antibodies (biotin-anti-PA or biotin-anti-LF) were characterized by HABA analysis for the degree of labeling and by immunoblot for functionality as previously described by Mukundan et al. Bioconj Chem. 2009, 20(2) 222-230, such description incorporated herein by reference.

For labeling of the reporter antibodies with photostable QDs, antibodies were buffer-exchanged from PBS to borate buffer (10 mM, pH 7.3) by using 10 kDa molecular weight cut-off (MWCO) spin filters. Carboxyl QD605 or QD655 stock (70 µl, 8 µM in borate buffer at pH 9.0) was diluted with 500 µl borate buffer (10 mM, pH 7.3), mixed with 200 µg anti-PA or anti-LF antibody, respectively. N-ethyl-N'-dimethylaminopropyl-carbodiimide (EDC) in aqueous solution (8.4 µl, 100 mM) was added and the reaction mixture was stirred gently at room temperature for 1.5 hours. The reaction was quenched by addition of borate buffer (500 µl, 50 mM, pH 9.0) and incubated at 4° C. overnight, then washed at least five times with 1 mL borate buffer (25 mM, pH 7.5) using 100 kDa MWCO membrane spin filter. The reaction mixture was then passed through a second 1000 kDa MWCO, spin filter to remove large aggregates, and the filtrate was concentrated using 10 kDa MWCO, with a final solution buffer exchange to pH 7.5. The concentration of QDs were measured based on absorbance of QD605 at 532 nm with $\epsilon_{532}=810,000$ $M^{-1}cm^{-1}$ and QD655 with $\epsilon_{532}=2,100,000$ $M^{-1}cm^{-1}$. The concentration of QD conjugated antibodies was measured using bovine serum albumin as standard and BCA™ as the working reagent. Antibody-QD conjugates were characterized by SDS polyacrylamide gel electrophoresis (12.5%) and agarose gel electrophoresis (1%) and visualized by fluorescence imaging. The molar ratio of antibody to QD in the conjugate was measured and is approximately 3:1. Purified QD labeled antibodies (anti-PA-QD605 and anti-LF-QD655) were used as fluorescence reporters in the assay.

Figure 2:
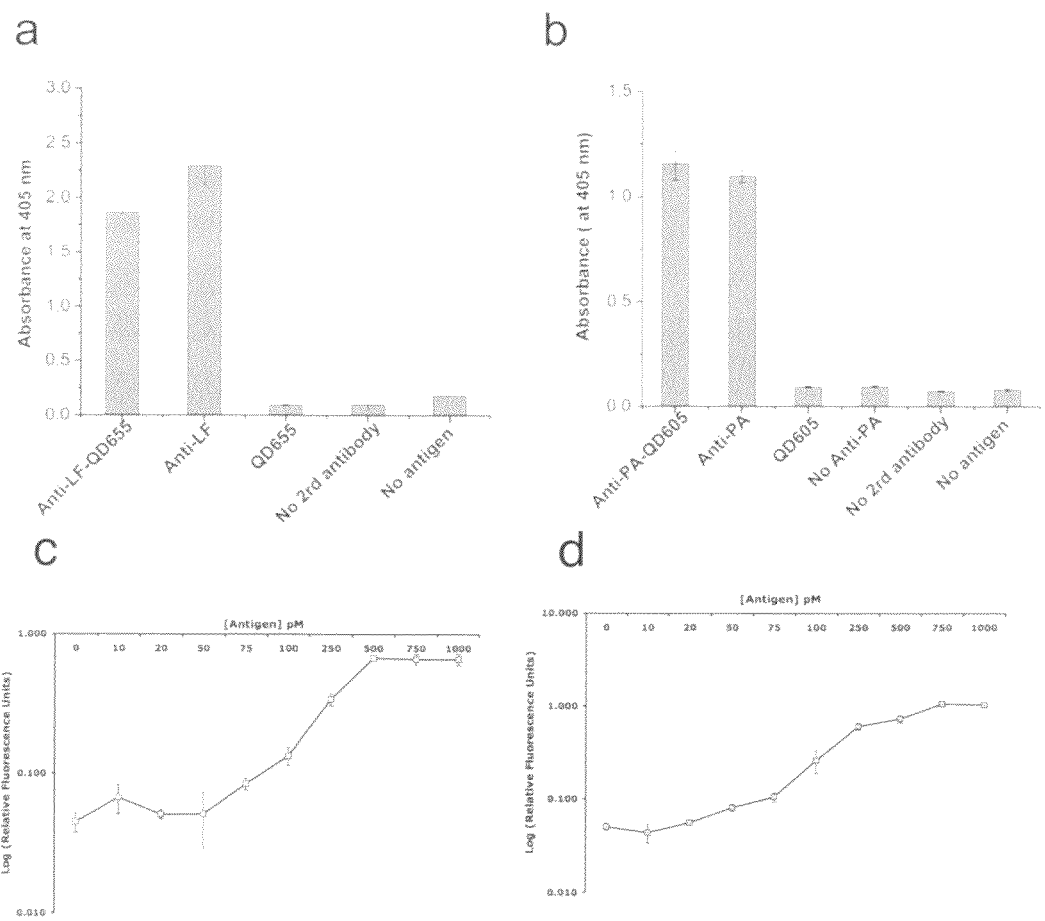
FIG. 2 shows activity assays for QD-labeled antibodies measured by traditional plate-based assays. Confirmation of activity of the QD-labeled antibody conjugates for LF (left) and PA (right) by enzyme-linked immunosorbent assays is shown in FIGS. 2a and 2b. In each case, non-specific binding associated with the QD alone, in the absence of the reporter (anti-HRP) antibody and the antigen were measured as controls. Binding of the antibodies to their respective antigens validates bio-activity of the labeled conjugate.

Evaluation of antibody functionality by plate-based immunoassay was as follows. Both indirect and sandwich immunoassays were performed to assess antibody function and sensitivity. For enzyme linked indirect immunoassay, 96-well Immunosorp™ plate wells were coated with PA or LF at a concentration of 2 µg/ml, and subsequently incubated wells with antiPA-QD605 and anti-LF-QD655 (100 nM) in PBS-tween 20 (0.1%) containing 4.5% fish gelatin. Following washing to remove any unbound reagents, anti-mouse HRP-conjugated species-specific secondary antibody was added (1:2000). Tetramethylbenzidine substrate was then added and absorbance measured at 405 nm with a plate reader. No-antigen, no primary antibody, no secondary antibody, and serum controls were also performed. These preliminary experiments confirmed bioactivity of the QD-labeled antibodies (FIGS. 2a and 2b).

For fluorescence-based sandwich immunoassays, 96-well plates were coated with the appropriate capture antibodies (see above, 100 nM) in PBS for 2 hours at 37° C. The plates were blocked with 4.5% fish gelatin in PBS-tween 20 (0.1%) for 1 hr at room temperature. The antigen (PA or LF) was then added at a concentration of 2.5 µg/ml. Following an overnight incubation at 4° C., the reporter antibodies (anti-PA-QD606 or anti-LF-QD655) were added at a concentration of 100 nM in PBS and incubated for 2 hrs. QD-associated fluorescence was measured post-wash using a Molecular Devices Gemini™ fluorescence plate reader. These experiments measured the efficacy of the QD labeled antibodies to detect PA and LF in a plate-based format, using the fluorescence readout. The limit of detection (LoD) was determined to be ~0.1 nM for both antigens (FIGS. 2c and 2d).

Figure 3A:
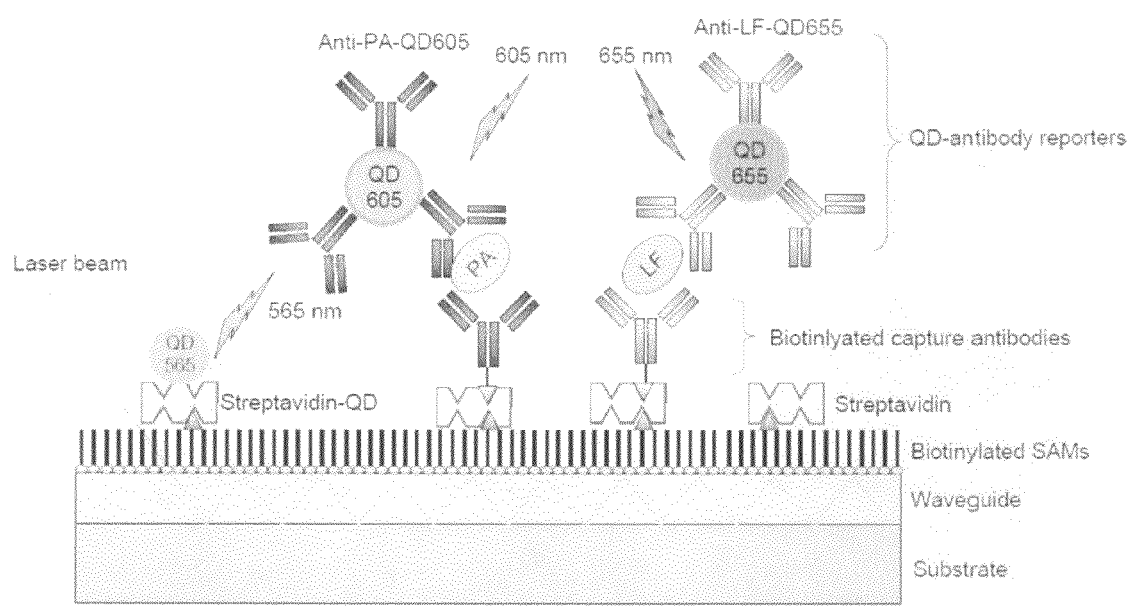
FIG. 3a. shows a schematic representation of the multiplex assay on a functionalized waveguide surface. The surface is functionalized with SAMs and biotinylated anti-PA and anti-LF capture antibodies, entrapped by biotin-avidin chemistry. Some of the streptavidin (10 pM) is labeled with QD565, for use as internal standard. Subsequent addition of the sample results in antigen (PA and LF) binding. Finally, the QD-labeled fluorescence reporters (anti-PA-QD605 and anti-LF-QD655) are added. Excitation at 535 nm results in differential emission of QDs, measured using the spectrometer interface. The multiplex spectrum obtained in a single sensing element upon detection of S-565QD, anti-PAQD605 and anti-LF-QD655 is shown in 3b. Black circles (•) represent the waveguide-background at that sensing element, which is a measure of intrinsic impurities associated with the waveguide itself. The triangles (Δ) indicate non-specific binding of control serum and the fluorescence reporter antibody to the functionalized waveguide surface in the absence of the antigen. Squares (□) indicate the specific signal associated with antigen (1 pM each)-reporter binding. A signal/noise of 3.9 for LF and 1.8 for PA is observed under these conditions. Standard curves for PA and LF on the waveguide-based sensor platform as a function of antigen concentration (3c). An LoD of 1 pM is achieved in serum, much better than the 100 pM reported with plate-based assays using the same materials (FIG. 2).
Figure 3B:
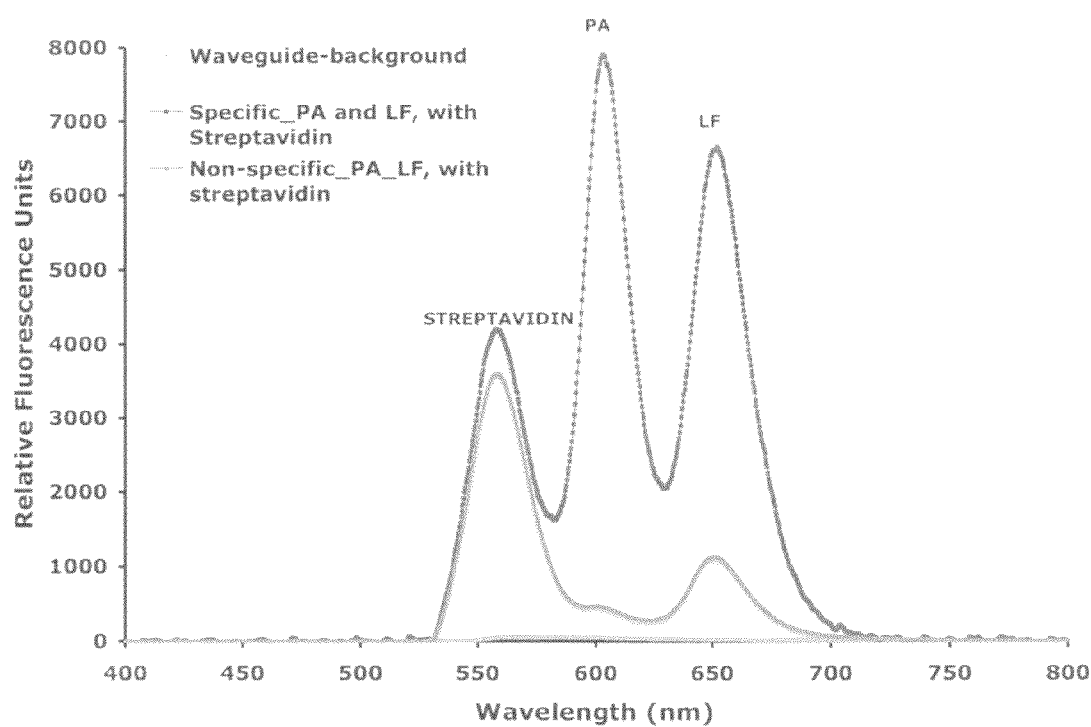

The multiplex detection of PA and LF on single channel waveguides and measurement of QD stability was as follows. Sandwich assays for PA and LF were individually optimized on the waveguide-platform before transitioning to the multiplex assay. A schematic representation of the multiplex assay is shown in FIG. 3a. Application of the assays to a multiplex format required optimization of QD-antibody pairs. Several factors such as antigen-antibody binding efficiency, quantum efficiency of the QD being used, QD size, number of antibodies conjugated on the QD surface, antibody conformation, stability of the conjugate, and assay sensitivity all affect assay performance. Preliminary experiments determined that conjugation of the anti-LF antibody with QD605 and the anti-PA antibody with QD 655 provided a relatively lower sensitivity in a multiplex format (data not shown). The multiplex assay format was optimized using antiPA-QD605 and anti-LF-QD655 conjugates as reporters and a typical measurement spectrum is shown in FIG. 3b. Kinetic measurements of antigen-antibody binding were also measured, as a function of antigen concentration. Based on these studies (data not shown), 10 minutes was determined as the optimal time for antigen-antibody incubation in this assay.

All experiments used a continuous wave 532 nm diode-pumped solid-state (5 mW, power coupled into the waveguide, 440 µW) frequency doubled Nd:YAG laser for excitation. The flow cell was assembled as described before. No blocking or stabilization were required with the use of SAMs as the functional surface. All injections were 200 µL volume and incubated for 10 minutes, followed by a wash with PBS containing 0.5% BSA. In both single and multichannel experiments, waveguide metrics were measured before actual sample addition. This included waveguide background (a measure of intrinsic fluorescence associated with the impurities in the waveguide itself), power coupled upon excitation (incident power is maintained at 440 µW) and the fluorescence signal associated with binding of the internal standard to the biotinylated SAM (SQD565, 10 pM). Once these measurements were made, the biotinylated capture antibody is added (b-anti-PA or b-anti-LF or both, 100 nM each). Subsequently, non-specific binding of control serum and the fluorescence reporter to the functional surface was measured (anti-PA-QD605 and/or anti-LF QD655). In multiplex experiments, the two fluorescent reporters were added sequentially (10 min incubation each) instead of together in order to overcome differences in measurement associated with variable diffusion of the two antibodies. A separate set of experiments were performed (data not shown) to show that repeat addition of the fluorescence reporter (5×) does not result in further increase in non-specific binding. Measurement of non-specific binding was followed by the addition of the antigen (PA or LF or both, depending on the experiment) at variable concentrations determined by the experiment (1 pM-1 nM). Following a 10 minute incubation, the reporter antibody was added again and the fluorescence signal associated with specific binding of the antigen to the antibody was measured using the spectrometer interface. Data were reported as relative fluorescence units. For comparison of data between waveguides, the S-QD565 was used as an internal standard for normalization.

Figure 3C:
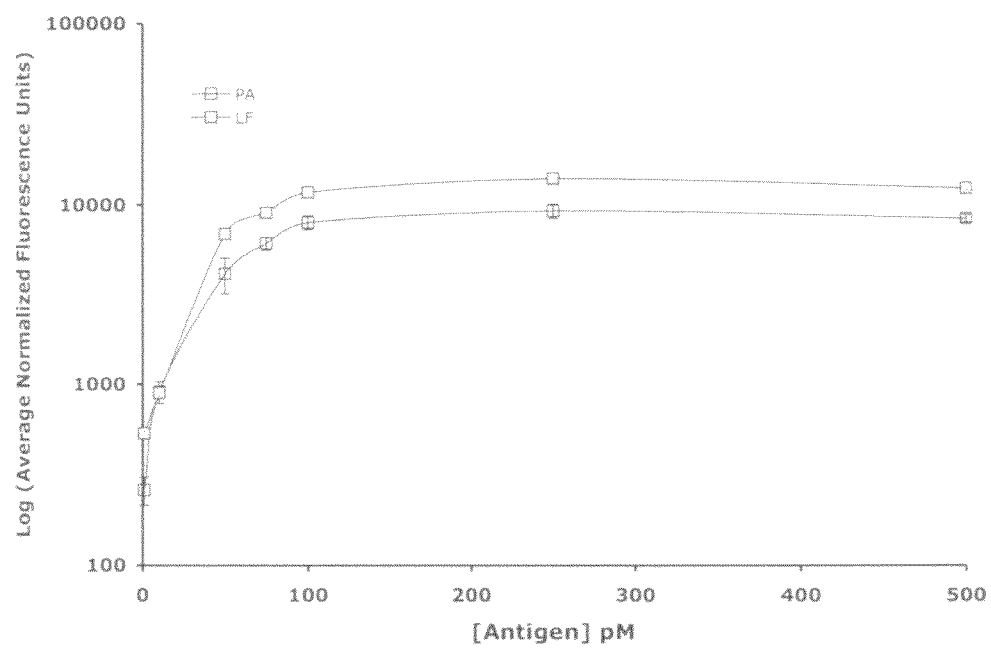

Standard curves for PA and LF were generated on different waveguides in order to overcome any effect of differential diffusion of the QD-labeled antibodies and a linear binding on an already modified functional surface (FIG. 3c). S-QD565 internal standard was used for normalization and data comparison between different waveguides. The LoD for each antigen was found to be 1 pM in serum (FIGS. 3c and d).

Measurement of S-QD565 (Internal Standard) on multichannel waveguides was as follows. Initial experiments to evaluate the performance of these waveguides involved the measurement of streptavidin-biotin binding. After assessing system metrics, S-QD565 (10-100 pM, depending on the experiment) was injected in all three-flow channels and the specific signal was measured (data not shown). These measurements were repeated with streptavidin labeled with QDs of varying emission (and hence, size). Preliminary measurements were made to ensure that there was no effect on diffusion of the sample across the flow cell (data not shown). For instance, the streptavidin signals associated with channel A1 were not significantly different from those observed in channel A4. Also, reversing the flow cell orientation by changing the injection port did not affect results (data not shown). In all experiments presented in this manuscript, the samples were injected in the orientation shown in FIG. 1.

Multiplex detection of PA and LF on the multichannel waveguide was as follows. The assay design and concentrations of reagents used for the multichannel experiments are the same as that outlined for single channel earlier. The following experimental matrix was used. Sandwich immunoassays for PA alone were performed in flow channel B with the SQD565 internal standard, whereas that for LF alone were performed in flow channel C. Flow channel A alone was used for multiplex detection of both antigens in the presence of the standard.

Evaluation of antibody functionality by plate-based immunoassay was as follows. The detection of PA and LF by plate-based indirect and sandwich immunoassay is shown in FIGS. 2a and b. The indirect immunoassay used a colorimetric detection approach for measurement of PA and LF and simply allowed for the conformation of the bio-activity of the QD-labeled antibody. Concentration-dependent detection of PA and LF was determined in a fluorescence-based sandwich immunoassay (FIGS. 2c and d) and the LoD was determined to be 100 pM in serum for each antigen using this approach.

Optimization of the assay and generation of standard curves was as follows. The multiplex assay was optimized for speed, sensitivity, quantum efficiency of the QDs and other parameters. For example, initial iterations of the assay used an anti-LF antibody conjugated to QD605. However, the diminished quantum efficiency of QD605 and the poor binding affinity of the antibody resulted in a poor signal/background (data not shown). The anti-PA reporter antibody has an inherently better binding affinity to the antigen, as was determined by plate-based assays. Therefore, combining the antibody with the better binding affinity with the QD with poorer efficiency may still result in a significant signal resolution in the assay. Following this reasoning, in subsequent experiments, the anti-LF antibody was conjugated to QD655, greatly improving the signal/background. Also, assay conditions (buffers, incubation times, order of injection) were altered to enhance the performance of the LF assay. The optimized assay, using anti-LF-QD655 and anti-PA-QD605 is indicated in FIG. 3b. This assay format was used in all subsequent experiments.

QDs are inherently more photostable than organic dyes. Experiments performed in our laboratory have shown that repeat excitation (440 µW incident power, 3 second integration) of the anti-PA-QD655 reporter antibody results in a stable signal, with no decrease after 5 excitations, whereas the signal associated with its organic dye (AlexaFluor-647) labeled counterpart is completely photobleached under these conditions (data not shown). This photostability is essential for quantitative multiplex assays using our approach as multiple excitations must be used to measure laser light in-coupling via the internal streptavidin standard (below).

FIG. 3b demonstrates the raw spectra observed for the simultaneous detection of 1 pM of PA and LF with the S-565QD control (10 pM) in a single element of the multichannel waveguide. The waveguide-associated background is minimal (~100 RFU). The non-specific background associated with the LF antibody (2691 RFU) is much higher than that observed with PA (405 RFU). Yet, the specific signal observed with antigen binding is higher (10619 RFU for LF and 703.2 RFU for PA) at 1 pM of each antigen. A signal/non-specific binding of 3.9 for LF and 1.75 for PA is observed. The limit of detection (LoD) of PA and LF on the multichannel waveguide in serum is thus 1 pM. Concentration-dependent responses for PA and LF were then determined on individual waveguides (FIG. 3c). Because of the inherent differences in the waveguides and functional surfaces, 100% linearity in response is not expected.

Sandwich immunoassays for the efficient detection of anthrax lethal toxins such as PA, LF and edema factor are available but have a lower sensitivity than the presently described assay (compare Mourez et al., Nat Biotechnol. 2001, 19(10), 958-961). In addition, these assays were not performed in complex samples like serum, which can result in higher non-specific binding and a compromised signal/noise in plate-based assays.

Detection of streptavidin-QDs on the multichannel waveguide was as follows. A schematic representation of the design of the multichannel waveguide and a photograph of the same are shown in FIG. 1. Preliminary measurements of waveguide function were performed by injecting streptavidin-QD655 at 100 pM concentrations in buffer along the three flow channels. System metrics (in-coupled power, waveguide grating associated background and streptavidin signal) were measured in each of the 12 channels. A prototype data set in Table 1 shows consistency in measurement across the channels. The measurements were repeated with the injection channel reversed and using multiple QD-labeled streptavidin (data not shown) and a consistent data set was obtained. The multichannel waveguide was then used for the sandwich measurement of PA and LF.

Figure 4A:
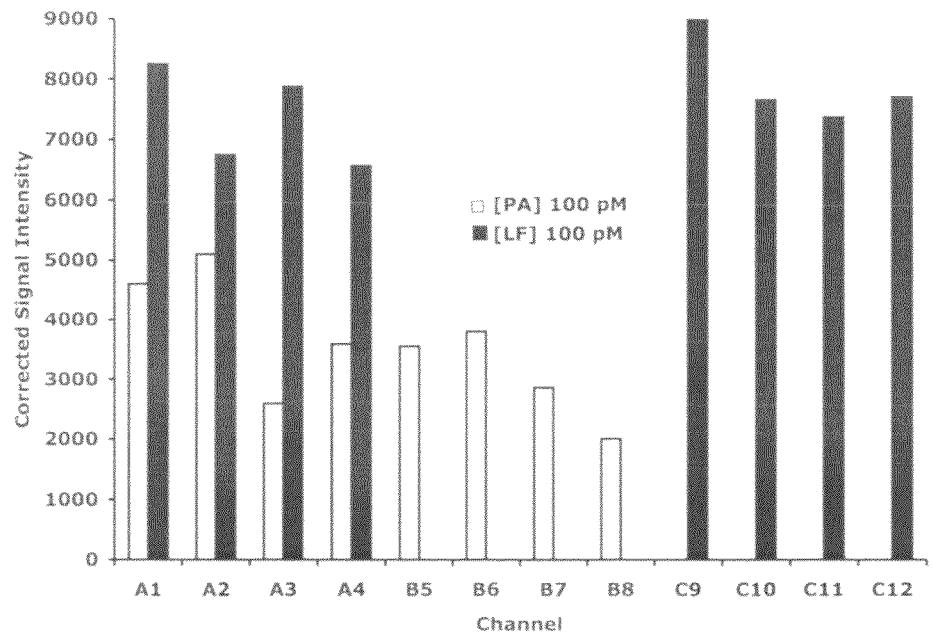
FIG. 4 shows maximum signal intensity observed at 676 nm in all 12 grating elements with the specific detection of 100 pM of PA/LF (or both) without normalization to the streptavidin standard is shown in FIG. 4a. The data is corrected for non-specific binding associated with the fluorescent reporter antibody and control serum. Both PA and LF were measured in channel A. Only PA was measured in channel B and only LF was measured in channel C. Although a positive detection is achieved at this concentration in all 12 sensing elements, there is a significant variation in the signal observed. This variation is significantly reduced by normalization to the S-QD565 internal standard (FIG. 4b). The average signal intensity from each channel is plotted for PA (FIG. 4c) and LF (FIG. 4d). There is no significant difference in the observed data. (student T-test, p>0.05, (n=4).
Figure 4B:
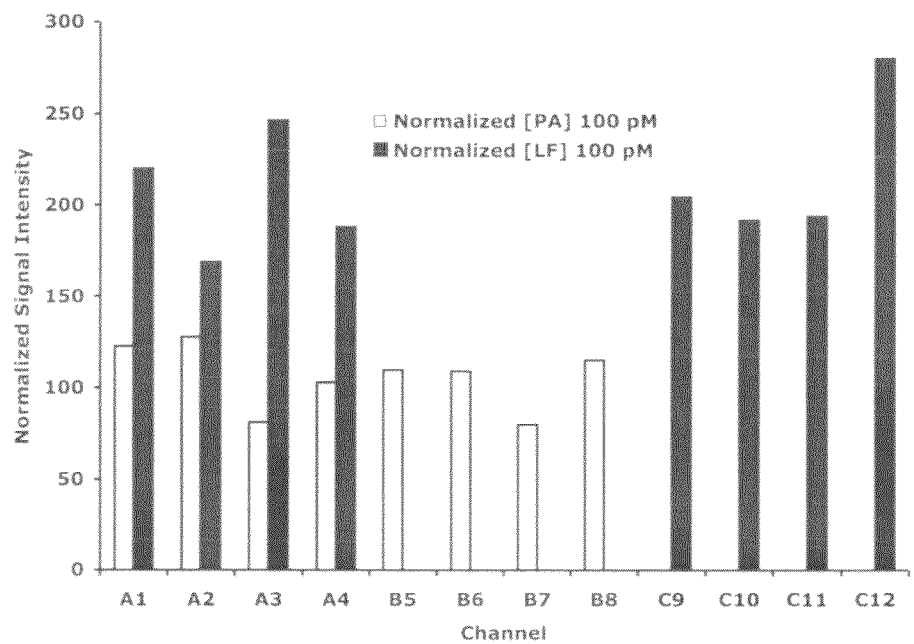
Figure 4C:
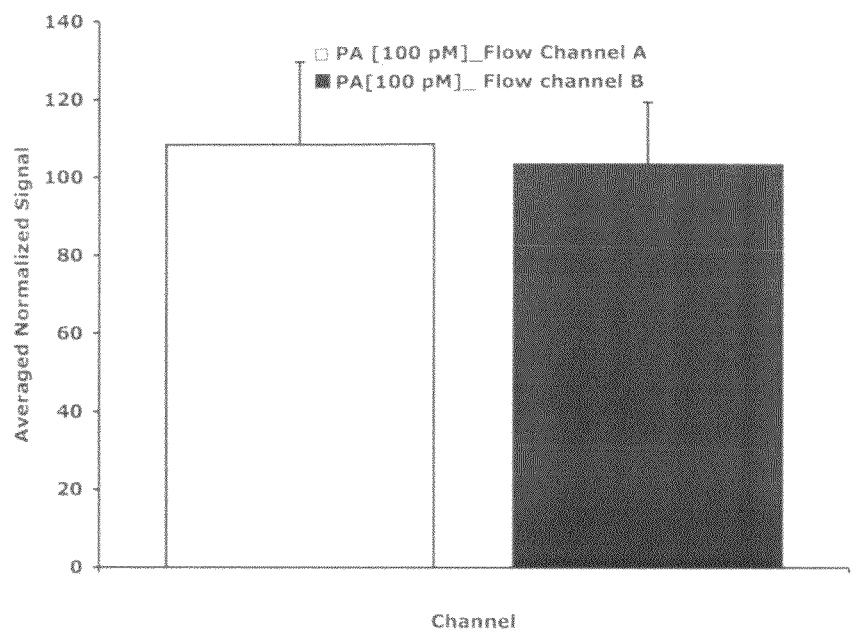
Figure 4D:
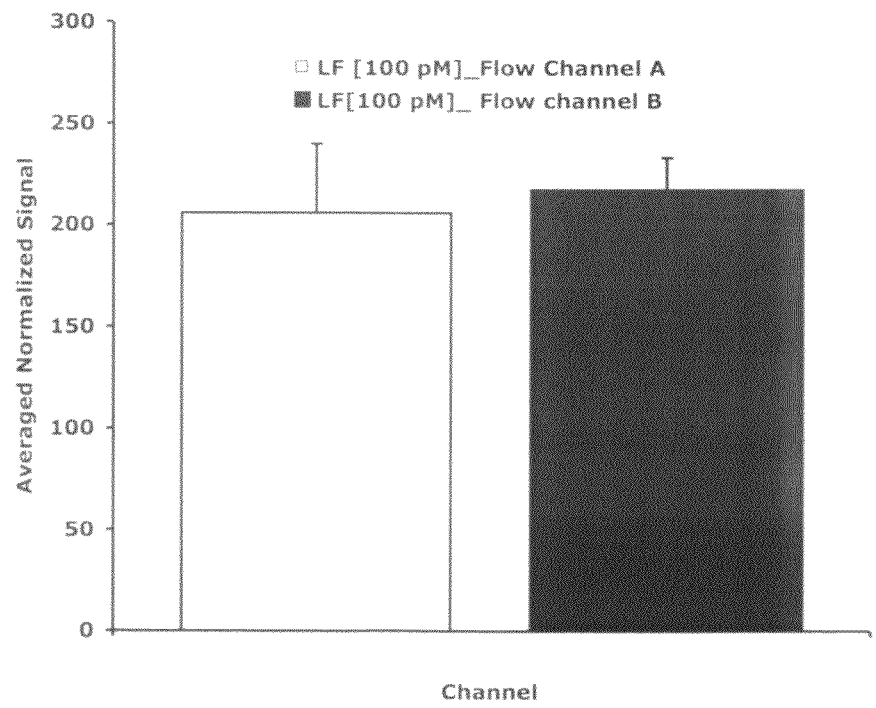

Multiplex quantitative detection of PA and LF in serum using multichannel waveguides was as follows. Multiplex immunoassays were performed on the multichannel waveguide for the simultaneous detection of PA and LF in serum as outlined earlier. The signals measured for the detection of 100 pM PA/LF in each of the sensing elements of the multichannel waveguide, without normalization for inter-assay variability, is shown in FIG. 4*a*. This assessment was performed because waveguides are intrinsically different from each other with respect to their fabrication, ability to couple light, and refractive index. Also, the functional properties of the waveguide vary slightly with the SAM coating in the individual gratings. Hence, the observed RFU values are expected to be very different between waveguides, and within the different sensing elements of the same waveguide. The signal intensity of S-QD565 also varies depending on the power coupled into the particular sensing element and the efficiency of SAM coating and hence, can be used for normalization of the inter- and intra-assay variability. As indicated in FIG. 4*b*, much of the variability is lost when the measured signal intensities are normalized to the S-QD565 signal within that element. As indicated in FIGS. 4*c* and 4*d*, the average measurements of PA and LF in serum across the different sensing elements are not significantly different from each other, validating the applicability of this approach for reproducible measurement of multiple samples.

These results are but the first step towards the application of multichannel waveguides to multiplex biodetection of real-world samples. Currently, SAM deposition, gasket preparation, and flow cell assembly are done manually, which requires precision and skill. It is anticipated that automating these processes in the future can facilitate the easy adaptation of this technology to medical diagnostics.

Quantitative, sensitive, specific, and rapid detection of pathogen biomarkers in complex patient samples will facilitate early detection of disease, and will allow medical professionals to track the course of the disease. The present invention describes a step in this direction by developing multiplex detection assays on multichannel waveguides for a limited suite of disease biomarkers in complex samples. Specifically, what has been found includes: a) methods for the conjugation of antibodies to polymer-coated QDs with excellent control of the antibody-QD ratio, and stability of these conjugates at neutral pH for bio-applications, b) a multiplex assay for *B. anthracis* PA and LF in serum using QDs as the fluorescence reporter, with a superior LoD than is achievable with traditional plate-based assays (FIGS. 2 and 3), c) design, fabrication and development of multichannel waveguides for the detection of a limited suite of biomarkers in multiple samples (FIG. 1), d) successful evaluation of the multichannel waveguide for the simultaneous detection of PA and LF in serum, with no compromise in sensitivity by using a complex biological matrix and e) use of S-QD565 as an internal standard for optimization of inter- and intra-assay variability. This approach can be used for a wide variety of pathogen biomarkers, secreted in the host, as well as for malignant disease markers. The waveguide-design, fabrication, and use can be modified to facilitate a higher throughout of samples with relative ease. Further efforts could improve gasket design and flow-cell construction to facilitate the application of the multichannel waveguide to evaluation of disease biomarkers in infected samples from actual patients.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A chip for use in simultaneous detection and quantitative measurement of multiple biomolecules, the chip comprising: a substrate, a patterned waveguide upon said substrate, a film layer upon the patterned waveguide, a reference biomolecule including an attached inorganic fluorescent reporter molecule, the reference biomolecule attached to said film layer as an assay element standard, and an amount of at least two recognition ligands attached to said film layer for capture of at least two differing target biomolecules.

2. A multichannel structure for use in simultaneous detection and quantitative measurement of multiple biomolecules comprising:

a substrate having at least one fluid channel therein wherein each fluid channel has at least two sensing element regions per channel, said multichannel structure further including a light absorbing material situated around each individual sensing element region thereby essentially eliminating cross-talk coupling between sensing element regions, each sensing element region having: (a) a film layer upon the substrate and (b) a reference biomolecule including an attached inorganic fluorescent reporter molecule, the reference biomolecule attached to said film layer as an assay element standard; and, at least one additional recognition ligand attached to said film layer for capture of a target biomolecule having at least two binding sites.

* * * * *